US006537255B1

(12) United States Patent
Raines

(10) Patent No.: US 6,537,255 B1
(45) Date of Patent: Mar. 25, 2003

(54) HUBER NEEDLE WITH FOLDING SAFETY WINGS

(75) Inventor: Kenneth C. Raines, Bethlehem, PA (US)

(73) Assignee: B Braun Medical, Inc., Bethlehem, PA (US)

( * ) Notice: Subject to any disclaimer, the term of this patent is extended or adjusted under 35 U.S.C. 154(b) by 0 days.

(21) Appl. No.: 09/685,825

(22) Filed: Oct. 9, 2000

(51) Int. Cl.[7] ................................................ A61M 5/32
(52) U.S. Cl. ........................ 604/177; 604/263; 604/192
(58) Field of Search .................................. 604/162, 192, 604/177, 197, 198, 165.03, 164.04, 263, 164.07, 164.08

(56) References Cited

U.S. PATENT DOCUMENTS

| | | | |
|---|---|---|---|
| 4,235,234 A | 11/1980 | Whitney et al. | 128/216 |
| 4,611,382 A | 9/1986 | Clark | 29/450 |
| 4,627,842 A | 12/1986 | Katz | 604/177 |
| 4,631,058 A * | 12/1986 | Raines | 604/177 |
| 4,645,495 A | 2/1987 | Vaillancourt | 604/180 |
| 4,676,783 A | 6/1987 | Jagger et al. | 604/171 |
| 4,710,176 A * | 12/1987 | Quick | 128/DIG. 26 |
| 4,735,618 A | 4/1988 | Hagen | 604/192 |
| 4,813,939 A | 3/1989 | Marcus | 604/177 |
| 4,820,282 A | 4/1989 | Hogan | 604/263 |
| 4,867,172 A | 9/1989 | Haber et al. | 128/763 |
| 4,888,001 A | 12/1989 | Schoenberg | 604/162 |
| 4,898,589 A | 2/1990 | Dolgin et al. | 604/198 |
| 4,909,792 A | 3/1990 | Norelli | 604/192 |
| 4,935,011 A | 6/1990 | Hogan | 604/177 |
| 4,935,013 A | 6/1990 | Haber et al. | 604/192 |
| 4,941,881 A | 7/1990 | Masters et al. | 604/162 |
| 4,944,731 A | 7/1990 | Cole | 604/192 |
| 4,950,249 A | 8/1990 | Jagger et al. | 604/192 |
| 4,950,250 A | 8/1990 | Haber et al. | 604/192 |
| 4,969,876 A | 11/1990 | Patterson | 604/171 |
| 5,011,479 A | 4/1991 | Le et al. | 604/198 |
| 5,019,048 A | 5/1991 | Margolin | 604/153 |
| 5,085,639 A | 2/1992 | Ryan | 604/110 |
| 5,120,320 A | 6/1992 | Fayngold | 604/177 |
| 5,147,319 A | 9/1992 | Ishikawa et al. | 604/174 |
| 5,188,611 A | 2/1993 | Orgain | 604/192 |
| 5,192,275 A | 3/1993 | Burns | 604/263 |
| 5,295,972 A | 3/1994 | Mischenko | 604/192 |
| 5,312,368 A | 5/1994 | Haynes | 604/192 |
| 5,330,438 A | 7/1994 | Gollobin et al. | 604/177 |
| 5,350,368 A | 9/1994 | Shields | 604/263 |
| 5,354,281 A | 10/1994 | Chen | 604/177 |
| 5,356,387 A | 10/1994 | Sirbola | 604/198 |
| 5,486,163 A | 1/1996 | Haynes | 604/192 |
| 5,498,241 A * | 3/1996 | Fabozzi | 604/165.03 |
| 5,505,711 A | 4/1996 | Arakawa et al. | 604/171 |
| 5,531,704 A | 7/1996 | Knotek | 604/192 |
| 5,549,571 A | 8/1996 | Sak | 604/198 |
| 5,584,813 A | 12/1996 | Livingstonk et al. | 604/177 |
| 5,607,398 A | 3/1997 | Parmigiani | 604/177 |
| 5,674,201 A | 10/1997 | Steinman | 604/165 |
| 5,706,520 A | 1/1998 | Thornton et al. | 2/21 |
| 5,755,694 A | 5/1998 | Camus | 604/162 |
| 5,823,997 A | 10/1998 | Thorne | 604/110 |
| 5,879,330 A * | 3/1999 | Bell | 604/175 |
| 5,951,522 A * | 9/1999 | Rosato et al. | 604/162 |
| 5,951,525 A | 9/1999 | Thorne et al. | 604/198 |

OTHER PUBLICATIONS

Burron's Leaflet, Whin®—Winged Huber Infusion Needles.

* cited by examiner

Primary Examiner—Brian L. Casler
Assistant Examiner—Kevin C. Sirmons
(74) Attorney, Agent, or Firm—Christie, Parker & Hale, LLP

(57) ABSTRACT

A safety needle assembly has a needle with a pointed tip and at least one generally planar wing attached via a pivot pin to the needle. The wings are moveable between an unguarded position wherein the tip of the needle is exposed to facilitate insertion of the needle and a guarded position wherein access to the tip of the needle is inhibited so as to reduce the likelihood of inadvertent needle stick.

32 Claims, 8 Drawing Sheets

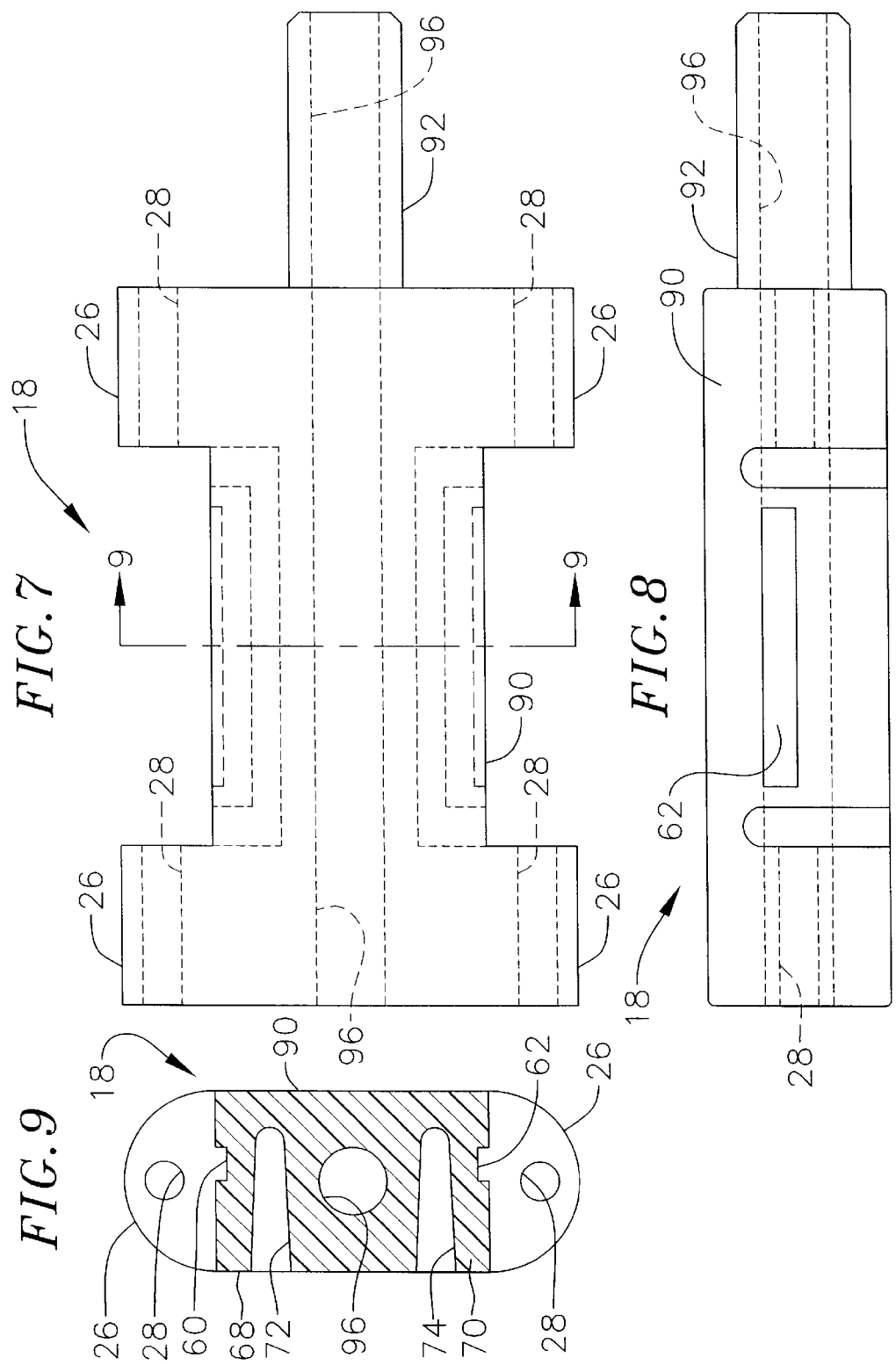

HUBER NEEDLE WITH FOLDING SAFETY WINGS

FIELD OF THE INVENTION

The present invention relates generally to hypodermic needles and relates more particularly to a 90° Huber needle having a pair of safety wings which fold around the needle so as to mitigate the likelihood of an inadvertent needle stick.

BACKGROUND OF THE INVENTION

Huber needles for accessing implanted vascular access ports are well known. Such Huber needles are frequently used to inject fluids used in chemotherapy or for the infusion of antibiotics or other medication via an implanted vascular access port. Huber needles are constructed to minimize coring which occurs with a conventional needle when it is inserted through an elastomeric septum (such as the septum of an implanted vascular access port) and a portion of the elastomer is cut away. It is important to use non-coring needles with implanted vascular access ports, since coring could lead to leakage from the access port and the resulting requirement that the port be replaced.

Contemporary Huber needles typically comprise a right-angle needle which extends from a hub, and two generally coplanar wings which typically extend outwardly, in a horizontal plane, from the hub. The wings are used to grasp and manipulate the Huber needle, as is discussed in detail below. Huber needles typically comprise a stainless steel needle having a 90° bend formed therein, with a sharpened tip formed at the needle's distal end and the hub formed at the proximal end. Tubing extends from the proximal end of the needle to facilitate fluid infusion. The wings, which extend in opposite directions from the hub, incorporate living hinges which are formed where the wings attach to the hub. The living hinges facilitate upward bending of the wings, such that the wings may be placed in generally parallel, laminar juxtaposition with one another and thus used as a handle during the needle insertion process.

A Huber needle is typically utilized to access an implanted vascular access port by bending the outwardly extending, generally horizontal wings upwardly such that they are generally parallel and laminarly juxtaposed with respect to one another and then grasping the two upwardly bent wings between the thumb and forefinger of one hand. The pointed tip of the Huber needle is then inserted through the skin and into the implanted vascular access port.

After insertion, the wings of the Huber needle are permitted to regain their generally coplanar configuration so that they lie generally flat upon the skin of the patient. The wings are then taped to the patient's skin to thereby prevent undesirable movement of the Huber needle during the injection process. Fluid is then injected through the Huber needle into the implanted vascular access port. After the desired amount of fluid has been injected into the access port, the Huber needle is untaped and the needle is removed from the injection site.

A problem commonly associated with hypodermic needles, including Huber needles, is that of inadvertent needle sticks. Once the needle is removed from the injection site, the needle may accidentally come into contact with some portion of the care giver's body, resulting in an inadvertent needle stick. It should be appreciated that merely scratching the skin with the unprotected sharp tip of a used needle may be sufficient to cause the transmission of a deadly and/or debilitating infectious disease, such as Hepatitis C or AIDS. Therefore, it is important to provide a means for reducing inadvertent needle sticks.

SUMMARY OF THE INVENTION

A safety needle assembly constructed according to practice of principles of the present invention comprises a needle having a pointed tip and at least one generally planar wing attached via a pivot pin to the needle. The wing or wings are moveable between an unguarded position, wherein the tip is exposed to facilitate insertion of the needle, and a guarded or shielding position, wherein access to the tip of the needle is inhibited to thereby substantially prohibit the likelihood of an inadvertent needle stick.

These, as well as other advantages of the present invention, will be more apparent from the following description and drawings.

BRIEF DESCRIPTION OF THE DRAWINGS

FIG. 7 is a semi-schematic plan view of the hub of the Huber needle of FIG. 1 (absent the structure for mounting the third wing);

FIG. 8 is a semi-schematic side view of the hub of the Huber needle of FIG. 1 (absent the structure for mounting the third wing);

FIG. 9 is a semi-schematic in-view of the hub of the Huber needle of FIG. 1 (absent the structure for mounting the third wing)

DETAILED DESCRIPTION OF THE INVENTION

The detailed description set forth below in connection with the appended drawings is intended as a description of a preferred embodiment of the safety needle assembly of the present invention and is not intended to represent the only form in which the safety needle assembly may be constructed or utilized.

Although the safety needle assembly of the present invention is described and illustrated herein as incorporating a 90°

Huber needle, those skilled in the art will appreciate that the safety needle assembly may incorporate various different types of needles or injection devices. Thus, discussion and illustration of the safety needle assembly of the present invention as incorporating a 90° Huber needle is by way of illustration only and is not by way of limitation.

As is described below in greater detail, the safety needle assembly of the present invention is configured to be withdrawn from a patient and placed in a needle guarding or shielding configuration with one hand, so as to substantially reduce the likelihood of an inadvertent needle stick.

Figure 1:
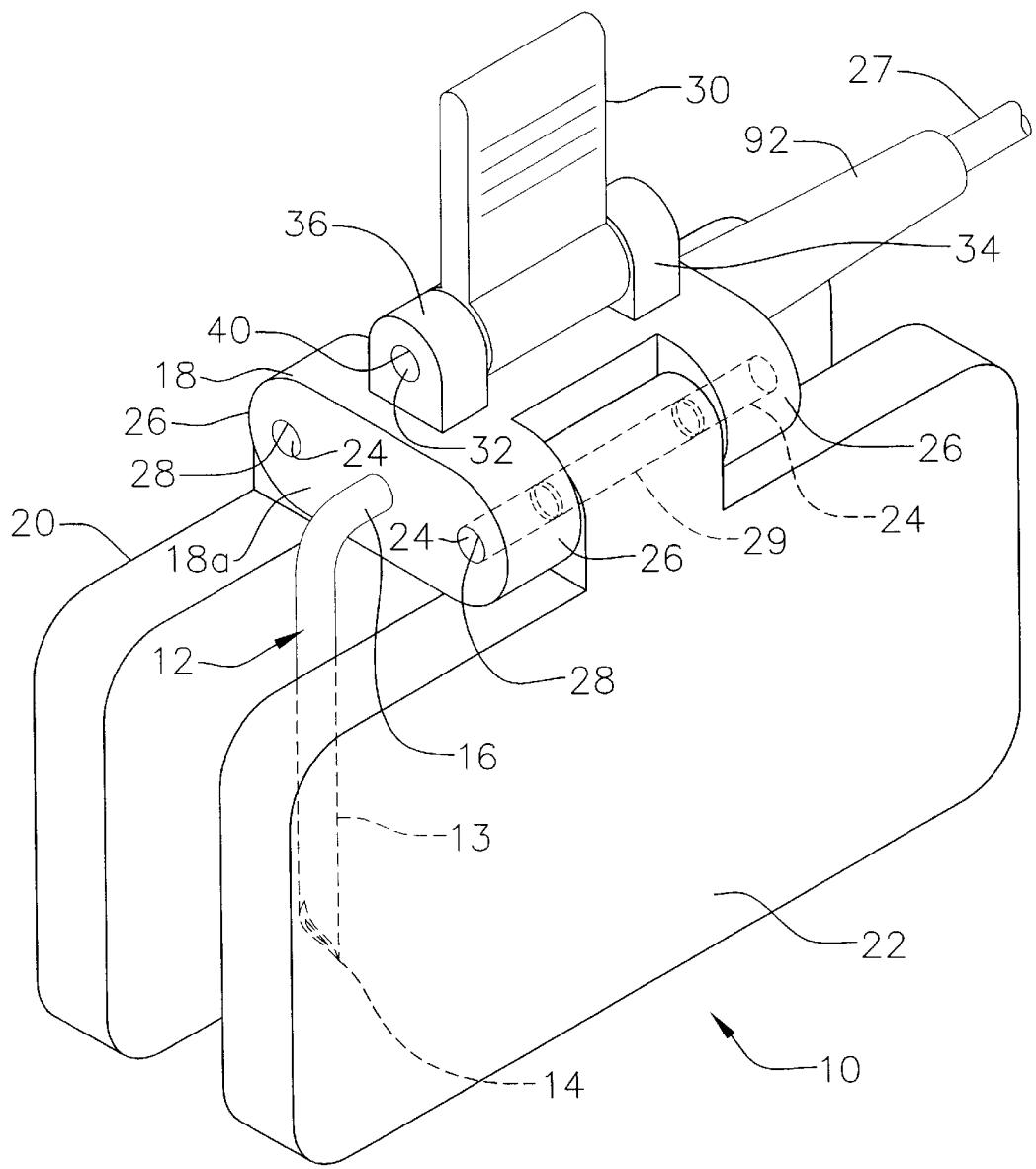
FIG. 1 is a semi-schematic perspective view of a Huber needle assembly with safety wings according to the present invention, showing the wings in a needle tip guarding or shielding position, wherein the wings are generally parallel with respect to one another.
Figure 2:
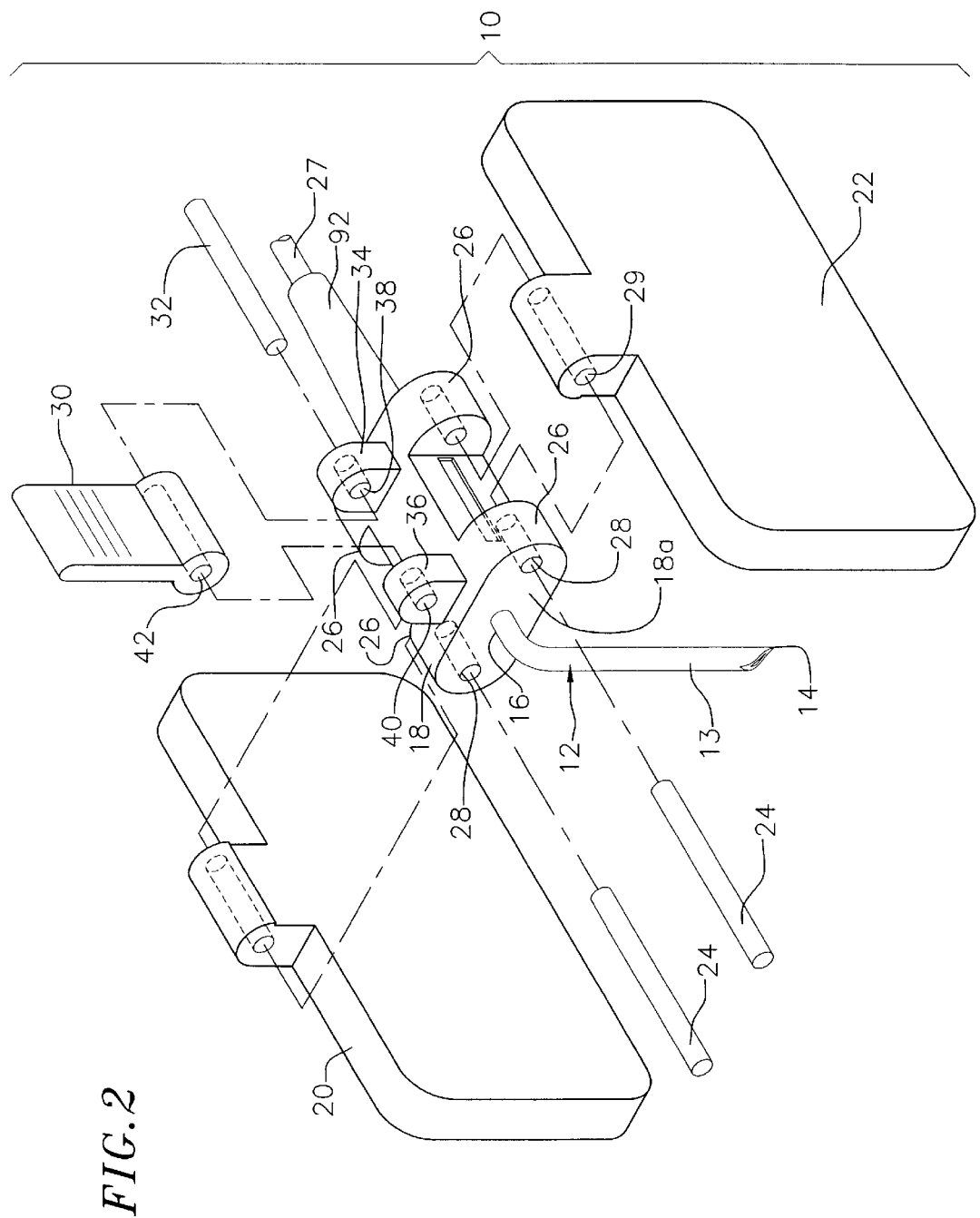
FIG. 2 is a semi-schematic exploded view of the Huber needle of FIG. 1.

Referring now to FIGS. 1 and 2, the safety needle assembly 10 comprises a needle, preferably a 90° Huber needle 12 comprising a vertically extending shaft portion 13 with a non-coring tip 14 on its distal end and a generally horizontally extending base or arm portion 16 on its proximal end. A hub 18 is on the base portion 16 and first and second wings 20 and 22, respectively, are hingedly or pivotally attached to the hub via pivot pins 24. The pivot pins 24 preferably each extend through bosses 26 which extend generally horizontally from the hub 18 and which have openings or bores 28 formed therein for receiving and frictionally engaging the pivot pins 24, such that the pivot pins 24 are held therein. The pivot pins 24 are received within bores 29 formed within the wings 20 and 22. The bores 29 are sized to mitigate friction with the pivot pins and therefore allow easy, low-friction movement of the wings 20 and 22 with respect to the hub 18, as is described in detail below. Tubing 27 is attached to the distal end of the base portion 16 of the needle 12, preferably via the hub 18, and is in fluid communication with the needle 12 to thereby facilitate injections via a syringe or infusion bag or the like.

The first and second wings 20 and 22 are preferably generally planar in configuration. As used herein, the term "generally planar" is defined to exclude wings which fold or pivot along the length or width to thereby define a plurality of wing portions which move out of a common plane with respect to one another. Thus, each of the first and second wings of one preferred embodiment of the present invention will generally define a plane, regardless of the position of the wing. Further, each of the wings has a generally planar or smooth upper surface to facilitate easy taping of the wing to a patient. Each of the wings preferably also has a generally planar or smooth lower surface to thereby mitigate any discomfort to the patient which may be caused by an uneven or non-smooth surface.

The entire safety needle assembly of the present invention, including any locking mechanisms for maintaining the wings in the guarded or shielding position, is smooth and configured to enhance patient comfort. Indeed, the present invention does not contain any downwardly extending protrusions which would tend to cause discomfort to the patient.

The needle 12 extends from the end 18a of the hub 18 in a manner which facilitates easy viewing and placement of the needle tip 14 into an implanted vascular access port. Such forward placement of the needle also facilitates easy viewing of the injection site during injection, to thereby assure proper operation of the safety needle assembly. Further, placement of the needle shaft portion 13 forward of the hub provides an added degree of safety, in that the tip of the needle is positioned further from the user's fingers.

Although it is preferred that the needle of the present invention extend forward of the hub as described above, it is understood that the pivoting wings of the present invention are likewise suitable for use in similar needle devices wherein the needle extends downwardly from a position proximate the center of the hub. Indeed, the present invention may find application in various different configurations of needle assemblies, wherein the needle extends from various different portions of the hub.

Figure 3:
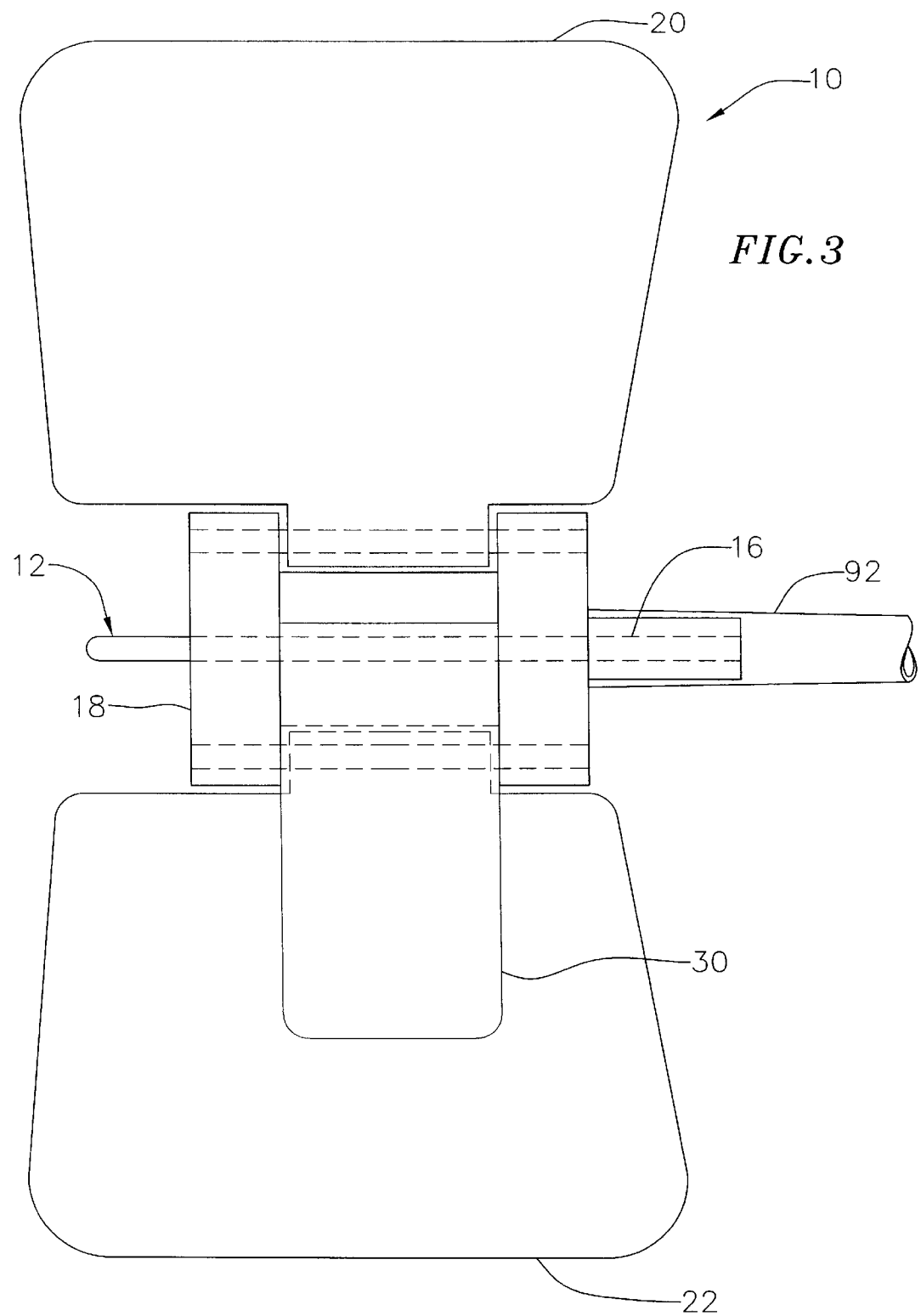
FIG. 3 is a semi-schematic plan view of the Huber needle of FIG. 1, showing the first and second wings in one unguarded position, wherein the wings are generally coplanar with respect to one another and showing a third wing folded over.
Figure 4:
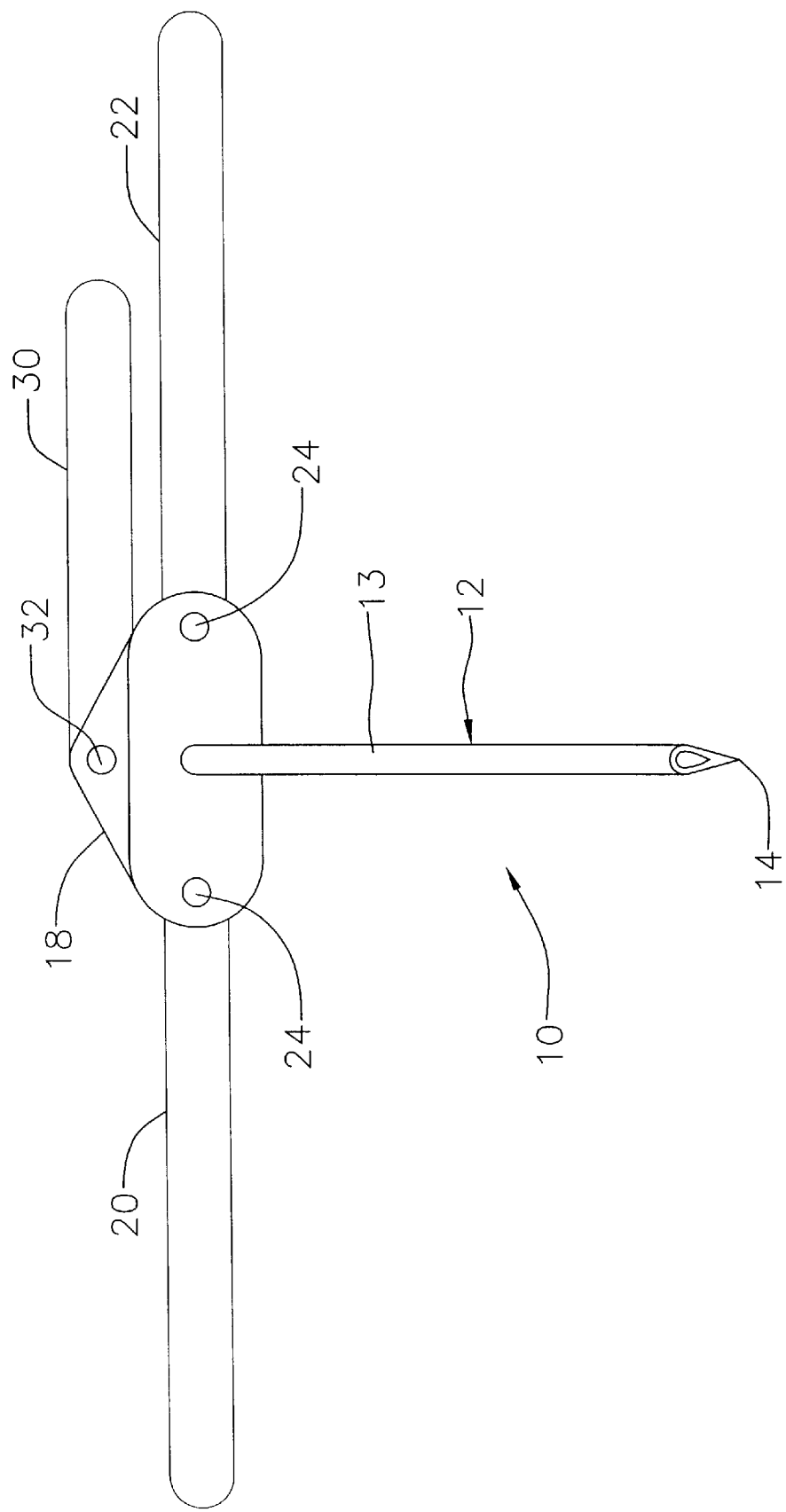
FIG. 4 is a semi-schematic end view of the Huber needle of FIG. 3.

Optionally, the safety needle assembly further comprises an auxiliary or third wing 30, which is preferably hingedly or pivotally attached to the hub 18 via pivot pin 32. The pivot pin 32 preferably extends through two bosses 34 and 36 which extend upwardly from the hub 18 and have openings 38 and 40 formed therein for receiving and frictionally engaging the pivot pin, such that the pivot pin is held therein. The pivot pin 32 is received within a bore 42 (FIG. 2) formed within the third wing 30. The third wing 30 may be rotated to a position where it extends upwardly from the hub 19 (as shown in FIGS. 1 and 2), or it may be rotated to a position where it lies generally flat (as shown in FIGS. 3 and 4). The bore 42 is preferably sized such that it does not substantially frictionally engage the pivot pin 32 to thereby allow the third wing 30 to be easily rotated from the upwardly extending position to the generally flat position thereof. Alternatively, the third wing may be integrally molded with the hub 18 such that it extends generally upwardly therefrom and does not move substantially to any other position.

As mentioned above, the pivot pins 24 which attach the wings 20 and 22 to the hub 18 are frictionally engaged within the openings 28 formed within the hub 18 and are received within the respective wing bores 29 such that the pins 24 do not substantially frictionally engage the bores 29. Therefore, each wing 20 and 22 freely rotates about its associated pivot pin 24 such that each wing readily falls or collapses from an outwardly extending, generally coplanar unguarded position (as shown in FIGS. 3 and 4) to a downwardly extending, generally parallel, guarded position thereof (as shown in FIGS. 1 and 2) under their own weight, i.e., due to the force of gravity. That is, when the safety needle assembly 10 is picked up by the third wing 30, for example, the first and second wings 20 and 22 tend to drop at least to approximately the guarded or shielding position, as shown in FIG. 1.

The hub 18, the first wing 20, the second wing 22, and the third wing 30 are preferably formed of molded plastic material, such as polymethylmethacylate, polycarbonate, and ABS (acrylonitrile-butadiene-styrene-terpolymer). The needle 12, the pivot pins 24, and the pivot pin 32 are preferably stainless steel. In one embodiment of manufacturing the safety needle assembly of the present invention, the hub 18 is insert molded onto the needle 12.

Referring particularly to FIGS. 3 and 4, the safety needle assembly is shown with the first and second wings 20 and 22 in the oppositely extending, generally horizontal, planar configuration, and the third wing 30 is shown folded over such that it is generally flat with respect to the first and second wings. In this generally flat configuration of the safety needle assembly 10, the first, second, and third wings may be taped to a patient's skin, proximate an injection site, so as to prevent undesirable moving and/or inadvertent removal of the needle 12 from the injection site.

Figure 5:
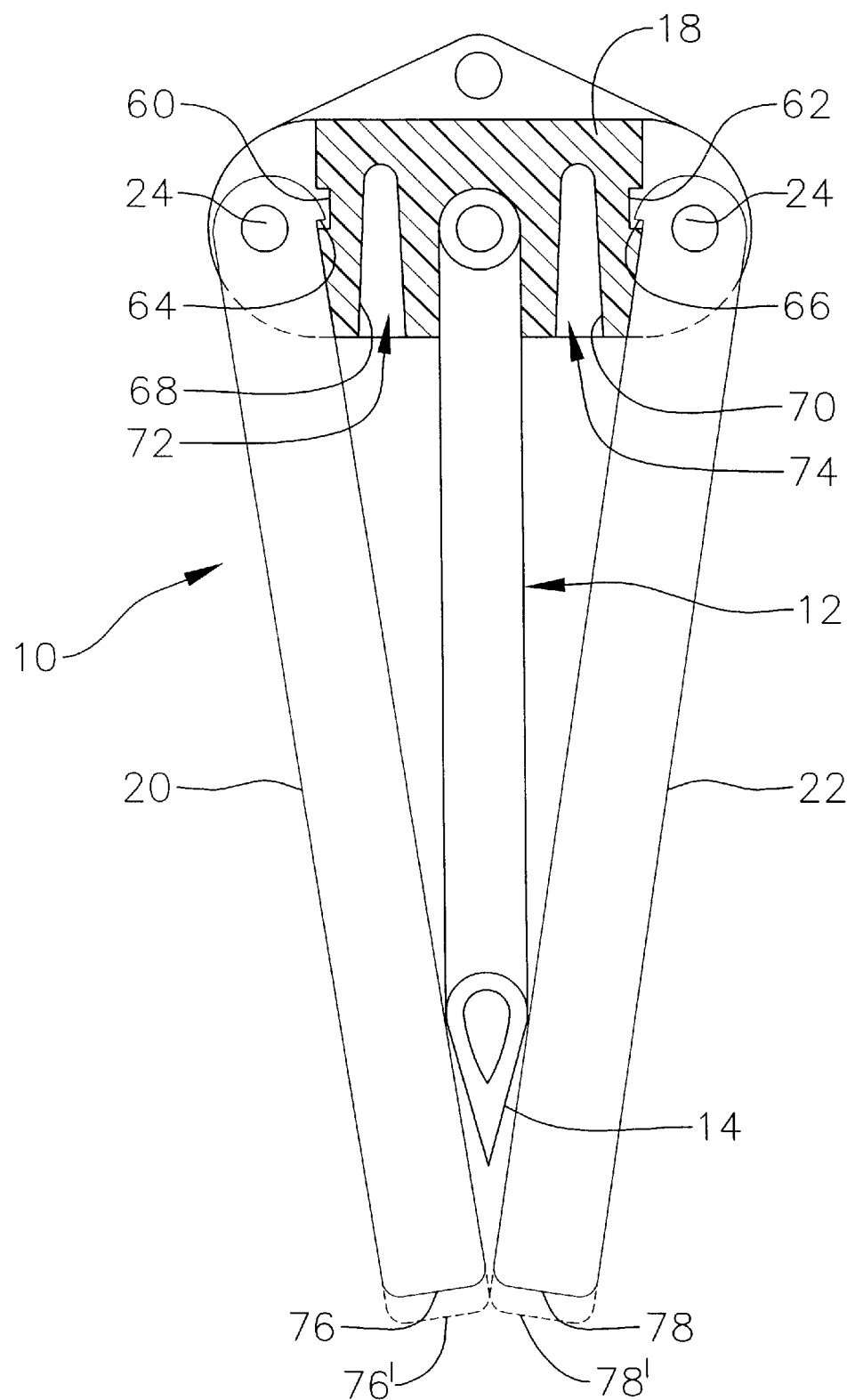
FIG. 5 is a semi-schematic end view, partially in section, of the Huber needle of FIG. 1, showing the wings locked in a needle tip guarding or shielding position, wherein the wings are generally parallel with respect to one another.

Referring now to FIG. 5, the first and second wings 20 and 22 are shown in their downwardly extending, generally parallel, guarded or shielding position. In this guarded position, the first and second wings are permanently locked into position with respect to the hub 18. Such locking is preferably facilitated by female detents 60 and 62, respectively, formed in the hub 18 and complementary male detents 64 and 66 formed at the proximal ends of the first and second wings.

Preferably, the first and second female detents 60 and 62 are formed upon downwardly extending, flexible flanges 68 and 70, respectively, which are defined by first and second channels 72 and 74, respectively, formed in the hub 18. The first and second female detents 60 and 62 are formed upon such flexible flanges to facilitate permanent locking of the first and second male detents 64 and 66 therein. As those skilled in the art will appreciate, the first and second flexible flanges readily deform or bend, to thereby accept the first and second male detents. That is, as the first and second wings are rotated from an unguarded position to the guarded position, the first and second male detents will cam against their respective flexible flanges 68 and 70 to cause the flexible flanges to bend inwardly sufficiently to permit the male detents 64 and 66 to engage and be received by the corresponding female detents 60 and 62.

As shown in FIG. 5, the distal ends or tips 76 and 78 of the first and second wings 20 and 22 preferably touch or almost touch (shown in phantom lines, 76' and 78') one another when in the guarded or shielding position. Thus, the pointed tip 14 of the needle 12 is well shielded by the first and second wings, to thereby reduce the likelihood of an inadvertent needle stick.

Figure 6:
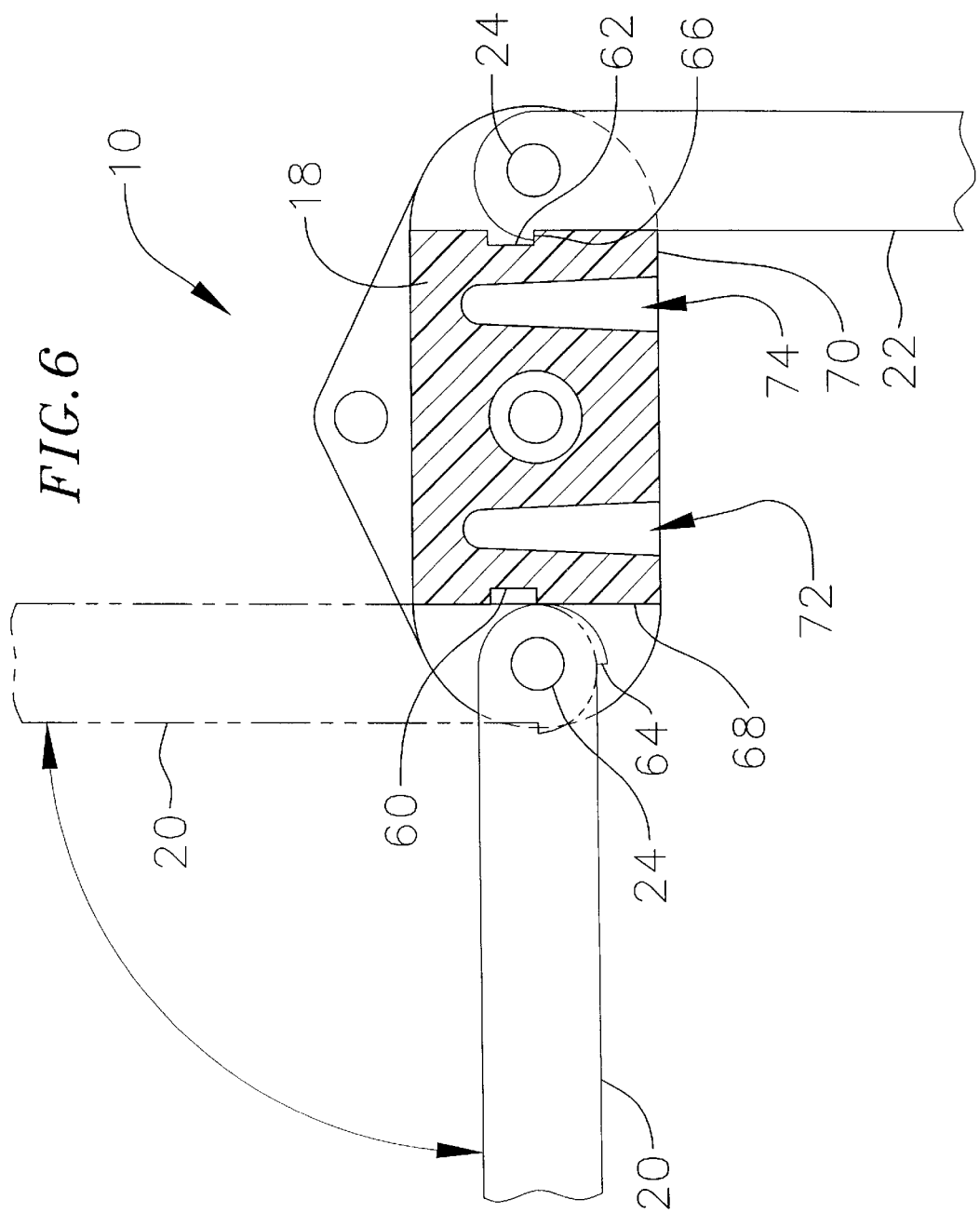
FIG. 6 is a semi-schematic enlarged end view of the Huber needle of FIG. 1, showing one wing in an unlocked, horizontally extending position (and showing the same wing in phantom extending upwardly) and another wing in a locked, downwardly extending position.

Referring now to FIG. 6, the first wing 20 is shown in a generally horizontal position, extending outwardly from the hub 18. The first wing 20 is also shown in phantom in a generally vertical position, wherein the first wing extends upwardly from the hub 18. Both the generally horizontal, outwardly extending position and the generally vertical, upwardly extending position of the first wing 20 define unguarded positions of the wing 20. Unguarded positions of the second wing 22 are similarly defined. Both the first and second wings 20 and 22 may be positioned such that they extend upwardly from the hub 18 so as to define a handle or grip with which the safety needle assembly 10 may be held during the insertion and or removal processes.

Referring now to FIGS. 7–9, the hub 18 preferably comprises a body 90 from which extends a tubing port 92 within which the flexible tubing 27 (shown in FIGS. 1 and 2) is received. The flexible tubing is preferably permanently attached to the hub 18 by thermally bonding the tubing in the bore 96 of the tubing port 92. A central bore 96, which is along the length of the hub body 90, receives and mounts the base portion 16 of the needle 12 (FIGS. 1–5).

Having described the structure of the safety needle assembly of the present invention in detail, it may be beneficial to describe its operation. Referring again to FIG. 3, the safety needle assembly 10 will generally be provided in a sterile package with the first and second wings 20 and 22 in the outwardly extending, generally coplanar, horizontal configuration to facilitate generally flat and volume-efficient packaging. The optional third wing 30, if provided, will preferably be in the folded over or flat position, as well. The optional third wing 30 may be folded over in either direction, as desired.

The first and second wings 20 and 22 will typically be folded or pivoted by the user into an upwardly extending, generally parallel configuration (such as is shown in phantom for the first wing 20 of FIG. 6). The upwardly extending wings 20 and 22 provide a means for gripping the safety needle assembly 10 during the insertion process according to well known principles. While holding the two upwardly extending wings 20 and 22 between the thumb and forefinger of one hand, the tip 14 of the needle 12 is inserted into the implanted vascular access port at the injection site. Once the needle 12 is fully inserted, the first and second wings are moved to their outwardly extending, generally coplanar position, as shown in FIGS. 3 and 4. The pivoting third wing 30, if provided, is similarly moved to a generally flat position. The first and second wings 20 and 22, as well as any third wing 30, may then be taped to the skin of the patient to inhibit undesirable movement and/or accidental removal of the needle 12 from the insertion site.

If a non-pivoting third wing 30 is provided, the non-pivoting third wing 30 (which is integrally formed to the hub 18, as discussed above) remains in the upwardly extending position thereof and the generally coplanar first and second wings 20 and 22 are taped to the skin of the patient.

After the needle assembly is in place in the vascular access port as described above, fluid is injected into the patient, as desired. When the injection process has been completed, the tape is removed and the needle 12 of the safety needle assembly 10 may be removed from the injection site. If an optional pivoting third wing 30 is provided, the third wing 30 is moved to the upwardly extending position thereof and is grasped (such as between a thumb and forefinger) to thereby facilitate removal of the needle 12 from the injection site. That is, the safety needle assembly 10 may be pulled away from the patient by holding the third wing 30 between the thumb and forefinger of one hand.

If no third wing 30 is provided, the safety needle assembly 10 may be pulled away from the patient by holding one or both of the first and second wings and/or the hub 18. If the safety needle 10 is pulled away from the patient by holding the first and/or second wings, the first and/or second wings will subsequently be released and the safety needle assembly 10 will then be held by the hub 18 (such as by the tubing port 92, FIG. 7) to thereby allow the wings to fall to the needle tip shielding position, as described in detail below.

As the safety needle assembly 10 is moved away from the patient, the first and second wings 20 and 22 will fall under their own weight to approximately the guarded or shielding position, as shown in FIG. 5. That is, the wings are preferably configured so as to have sufficient weight to cause the wings to fall from their generally coplanar, horizontally extending, unguarded position to their downwardly extending, generally parallel position. The above-described configuration of the first and second wings, in combination with the low friction pivotal attachment thereof to the hub, assures that the wings will drop as the safety needle assembly is picked up and moved away from the patient.

The first and second wings will tend to drop to a nearly parallel position, wherein the tips 76 and 78 are close to one another and preferably touch one another. The wings may be permanently locked into this guarded position as they fall under their own weight by the first and second male detents 64 and 66 engaging the respective first and second female detents 60 and 62.

When the wings do not lock into the guarded or shielding position under gravity, the fingers of the hand which is used for removal of the safety needle assembly 10 may be used to squeeze the wings together to thereby snap the first and second male detents into their corresponding first and second female detents to permanently lock the wings in the guarded or shielding position (FIG. 5). In this guarded and locked position, access to the pointed tip 14 of the needle 12 is prohibited. When the first and second wings are in their downwardly extending, generally parallel guarded position, the first and second wings may be parallel with one another, or may be nearly or generally parallel with respect to one another (at a slight angle, typically with the tips closer to one another than the opposite ends are to one another). In this guarded position, the wings prevent a finger, even the smallest finger of a hand, from entering therebetween and being stuck by the needle. Thus, use of the safety needle assembly 10 of the present invention substantially reduces the likelihood of an inadvertent needle stick. Furthermore, as is described above, once the wings are locked, they are permanently held in the locked position and cannot be moved. This ensures that the needle tip is shielded during the needle disposal process and thereby further contributes to the safety of the use of the needle assembly 10 of the present invention.

The first and second wings may fall, under their own weight, to an intermediate position, wherein the first and second wings are no longer generally horizontal, and wherein the first and second wings are not locked in the guarded position. Rather, the first and second wings may fall, under their own weight, to a position which is almost, but not quite, the locked position thereof. In this intermediate position, the first and second wings will not lock. Therefore, when the first and second wings fall to this intermediate position, it is necessary to move the first and second wings to the locked and guarded position thereof, as described above.

It is important to note that as the safety needle assembly is picked up or removed from a patient and the first and second wings fall to the guarded or shielding position, the first and second wings provide a degree of protection from inadvertent needle sticks whether or not the wings are locked. That is, the wings generally surround the sharp tip of the needle even though the wings are not locked into the guarded position and thus will tend to inhibit contact with the tip of the needle.

As mentioned above, using the same hand which is used for removal of the safety needle assembly 10 to effect locking of the first and second wings is advantageous in that it avoids the undesirable use of the opposite hand. As those skilled in the art will appreciate, use of the opposite hand substantially enhances the potential for an inadvertent needle stick.

In an alternative embodiment of the present invention, the first and second wings 20 and 22 are not fitted to the pivot pins 24 in a sufficiently loose manner to facilitate falling under their own weight as the safety needle assembly 10 is removed from the patient. In this embodiment, it will be necessary for the care giver to urge the first and second wings downwardly into the locked, guarded position, as shown in FIG. 5. Again, such urging of the first and second wings downwardly into the locked and guarded position is preferably performed with the same hand which is holding the safety needle assembly 10.

Figure 10:
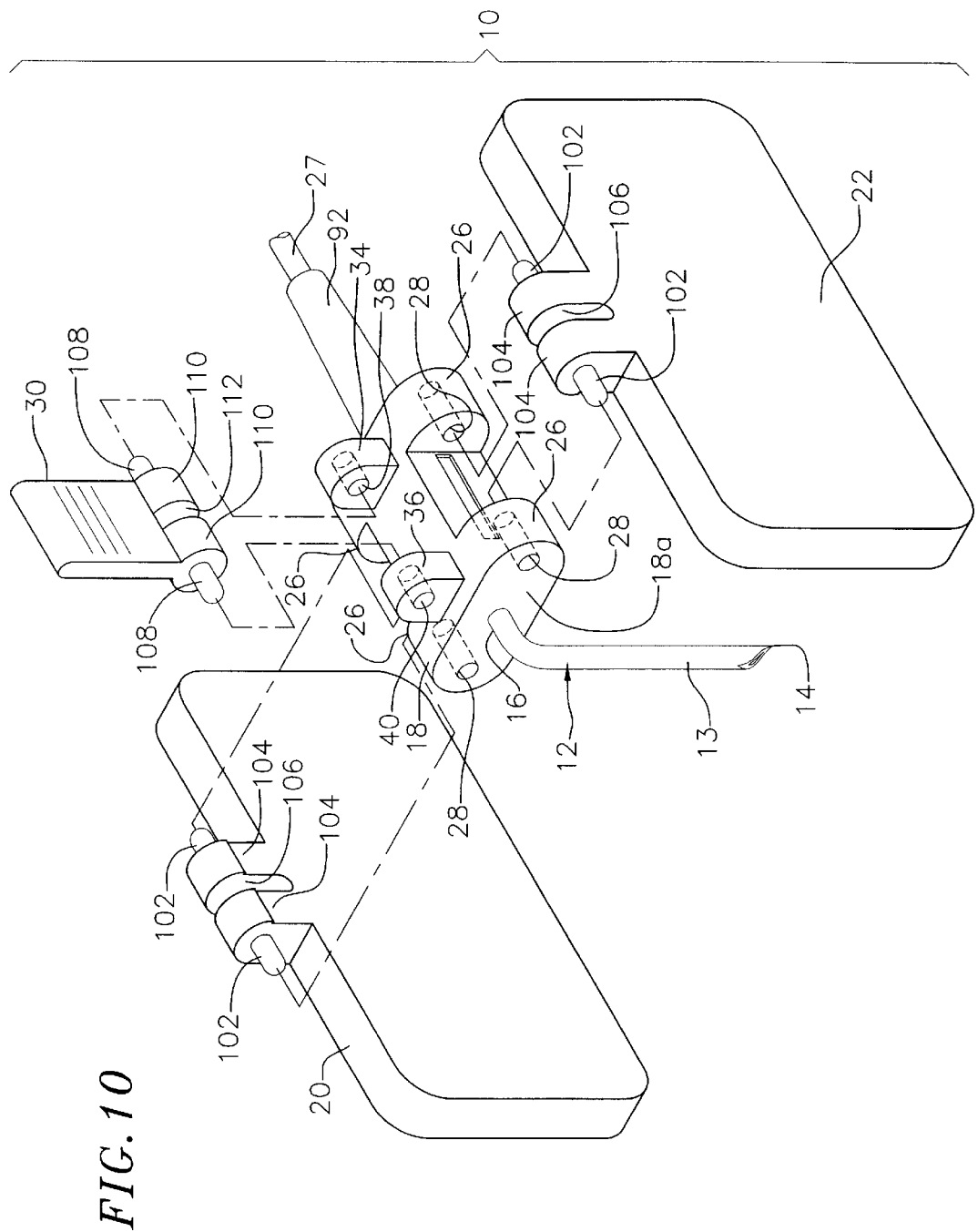
FIG. 10 is a semi-schematic exploded view of an alternative configuration of the Huber needle of the present invention.

Referring now to FIG. 10, according to an alternative configuration of the present invention, the pivot pins 24 and/or the pivot pin 32 (all best shown in FIG. 2) are replaced with integrally formed pins, 102 and 108, respectively, which facilitate low cost manufacturing and simplified assembly of the present invention.

More particularly, according to this alternative configuration of the present invention, each of the first and second wings, 20 and 22, comprises two upwardly extending, generally parallel posts 104 separated by a cut-out 106. Each post 104 has an outwardly extending pin 102 formed integrally therewith, for example by injection molding, and configured so as to be insertable within complimentary openings 28 formed in the hub 18. The pins 102 and the complimentary openings 28 are preferably formed such that they cooperate to facilitate movement of the first and second wings, 20 and 22, downwardly under their own weight, as discussed above. That is, the pins 102 are preferably sized so as to have a diameter which is substantially less than the diameter of the openings 28 of the hub 18.

The first and second wings, 20 and 22, are assembled to the hub 18 by squeezing the posts 104 of each wing toward one another (thereby reducing the size of the cut-out 106), such that the pins 102 may be received within the openings 28. One of the two pins 102 of each wing may be inserted into a corresponding opening 28 prior to insertion of the other pin 102 into its corresponding opening.

In a similar fashion, the third wing 30 is attached to the hub 18 via pins 108 extending outwardly from posts 110 formed thereto and separated from one another by cut-out 112.

Although pins formed to posts are described herein and illustrated in FIG. 10, those skilled in the art will appreciate that various other integrally formed attachment means (which eliminate the need for pivot pins 24 and/or 32) are likewise suitable.

It is understood that the exemplary safety needle assemblies described herein and shown in the drawings represents only the presently preferred embodiments of the invention. Indeed, various modifications and additions may be made to such embodiment without departing from the spirit and scope of the invention. For example, various different mechanisms for locking the wings 20 and 22 in the guarded position thereof are contemplated. Further, the wings may have various different shapes or configurations. However, it is important that the wings 20 and 22 adequately cover the tip 14 of the needle 20 so as to inhibit access thereto. Generally, it is preferred that the wings have generally flat lower surfaces to enhance the comfort of the patient during the injection process. Thus, these and other modifications and additions may be obvious to those skilled in the art and may be implemented to adapt the present invention for use in a variety of different applications.

What is claimed is:

1. A safety needle assembly comprising:
   a needle having a pointed tip; and
   at least one generally planar wing attached via a pivot pin to the needle, the wing(s) being movable between an unguarded position wherein the tip of the needle is exposed to facilitate insertion of the needle and a guarded position wherein access to the tip of the needle is inhibited so as to mitigate a likelihood of an inadvertent needle stick, and wherein the pivot pin is mounted in a spaced apart configuration from the needle.

2. The safety needle assembly as recited in claim 1, wherein the needle comprises a Huber needle.

3. The safety needle assembly as recited in claim 1, wherein the needle comprises a 90° needle.

4. The safety needle assemble as recited in claim 1, wherein the wing(s) comprises first and second wings.

5. The safety needle assemble as recited in claim 1, wherein the wing(s) comprises first and second wings, the first and second wings being generally coplanar and extending outwardly in generally opposite directions when in an unguarded position thereof and the first and second wings being generally parallel to one another with the tip of the needle disposed therebetween when the first and second wings are in the guarded position thereof.

6. The safety needle assemble as recited in claim 1, wherein the wing(s) comprises first, second and third wings, the first and second wings extending outwardly in generally opposite directions when in an unguarded position thereof, the first and second wings being generally parallel to one another with the needle disposed therebetween when the first and second wings are in the guarded position thereof and the third wing extending away from the needle so as to provide a grip during removal of the needle.

7. The safety needle assembly as recited in claim 1, wherein the wing(s) are moveable to an unguarded position which facilitates taping.

8. The safety needle assembly as recited in claim 1, further comprising a hub formed to the needle, the wing(s) being attached to the needle via the hub.

9. The safety needle assemble as recited in claim 1, wherein the wing(s) are configured such that the wing(s) are movable from the unguarded position to the guarded position thereof using one hand.

10. The safety needle assembly as recited in claim 1, wherein the wing(s) are attached to the needle such that the wings tend to fall due to gravity from an unguarded position thereof to the guarded position thereof when the needle is removed from an injection site.

11. The safety needle assembly as recited in claim 1, wherein the wing(s) are attached to the needle such that the wings fall due to gravity from an unguarded position thereof toward the guarded position thereof, but do not fall due to gravity completely to the guarded position thereof.

12. The safety needle assembly as recited in claim 1, further comprising a hub formed to the needle, the wing(s) being attached to the needle via a pivot pin attached to the hub.

13. The safety needle assemble as recited in claim 1, wherein the wing(s) are configured to lock in the guarded position thereof.

14. The safety needle assemble as recited in claim 1, wherein the wing(s) are configured to permanently lock in the guarded position thereof.

15. The safety needle assembly as recited in claim 1, further comprising:
- a hub formed to the needle, the wing(s) being attached to the needle via the hub;
- at least one first detent formed upon the hub;
- a complimentary second detent formed upon at least one of the wings; and
- wherein movement of at least one of the wings effects engagement of a first detent and a second detent so as to lock that wing in the guarded position.

16. The safety needle assembly as recited in claim 1, further comprising:
- a hub formed to the needle, the wing(s) being attached to the needle via the hub;
- at least one female detent formed upon the hub;
- a complimentary male detent formed upon at least one of the wings; and
- wherein movement of at least one of the wings effects engagement of a female detent and a male detent so as to lock that wing in the guarded position.

17. The safety needle assembly as recited in claim 1, wherein distal ends of two wings contact one another to inhibit access to the tip of the needle when the two wings are in the guarded position thereof.

18. The safety needle assembly as recited in claim 1, wherein the wing(s) are movable between an unguarded position wherein the tip of the needle is exposed to facilitate insertion of the needle and a guarded position wherein access to the tip of the needle is inhibited so as to mitigate a likelihood of an inadvertent needle stick, the wing(s) being attached to the needle in a manner which allows the wing(s) to fall from an unguarded position thereof to approximately the guarded position thereof under the force of their own weight as the needle is removed from an insertion site.

19. The safety needle assembly as recited in claim 1, further comprising a pin which extends through a portion of the hub and a portion of each wing for moveably attaching each wing to the hub.

20. The safety needle assembly as recited in claim 1, further comprising a stainless steel pin which extends through a portion of the hub and a portion of each wing for moveably attaching each wing to the hub.

21. A safety needle assembly comprising:
- a needle having a pointed tip and a base;
- a hub formed to the needle proximate the base thereof;
- first and second wings pivotally attached to the hub, the first and second wings being movable between an unguarded position wherein the tip of the needle is exposed so as to facilitate insertion of the needle and a guarded position wherein access to the tip of the needle is inhibited so as to mitigate a likelihood of an inadvertent needle stick, the first and second wings extending outwardly in generally opposite directions when in the unguarded position and the first and second wings being generally parallel to one another with the pointed tip of the needle disposed therebetween when in the guarded position thereof;
- a first detent member formed on each wing; and
- a complimentary second detent member formed on the hub for each first detent member, the first and second detent members configured to cooperate to permanently lock the first and second wings in the guarded position thereof.

22. The safety needle assembly as recited in claim 21, further comprising a third wing extending from the hub, the third wing being configured to facilitate grasping thereof when the needle is removed from an injection site.

23. The safety needle assembly as recited in claim 21, wherein the needle is a 90° Huber needle.

24. A method for performing an injection, the method comprising:
- inserting a needle having a horizontal arm into an injection site;
- injecting fluid through the needle;
- removing the needle from the injection site; and
- moving at least one generally planar wing from an unguarded position thereof wherein the tip of the needle is exposed to facilitate insertion of the needle to a guarded position thereof wherein access to the tip of the needle is limited so as to mitigate a likelihood of an inadvertent needle stick, wherein such generally planar wing is pivotally mounted in a spaced apart relationship from the horizontal arm of the needle.

25. The method as recited in claim 24, wherein moving the wing(s) from an unguarded position thereof to the guarded position thereof comprises moving the wing(s) from an unguarded position thereof to the guarded position thereof with one hand.

26. The method as recited in claim 24, wherein moving the wing(s) from an unguarded position thereof to a guarded position thereof at least partially occurs due to the wing(s) falling as the needle is removed from the injection site.

27. The method as recited in claim 24, further comprising taping the wing(s) proximate the injection site after inserting the needle.

28. The method as recited in claim 24, further comprising locking the wings in the guarded position thereof.

29. The method as recited in claim 24, further comprising taping first and second wings proximate the injection site.

30. The method as recited in claim 24, wherein removing the needle from the injection site comprises gripping a third wing and pulling the needle from the injection site.

31. The method as recited in claim 24, wherein moving at least one wing from an unguarded position to a guarded position thereof comprises moving first and second wings from an unguarded to a guarded position thereof.

32. The method as recited in claim 24, wherein moving at least one wing from an unguarded position to a guarded position thereof comprises moving first and second wings from an unguarded position to a guarded position thereof so as to permanently lock the first and second wings in the guarded position thereof.

* * * * *

UNITED STATES PATENT AND TRADEMARK OFFICE
CERTIFICATE OF CORRECTION

PATENT NO. : 6,537,255 B1
DATED : March 25, 2003
INVENTOR(S) : Raines

It is certified that error appears in the above-identified patent and that said Letters Patent is hereby corrected as shown below:

Title page,
Item [73], Assignee, delete "B Braun", insert -- B. Braun --.
Item [56], References Cited, U.S. PATENT DOCUMENTS, "5,584,813" reference, delete "Livingstonk", insert -- Livingston --.

Column 8,
Lines 31 and 66, delete "the needle, the wing(s)", insert -- the needle, the at least one wing --.
Lines 43, 45, 53 and 68 delete "assemble" insert -- assembly --.
Lines 44, 46 and 54, delete "wherein the wing(s)", insert -- wherein the at least one wing --.
Line 63, delete "wherein the wing(s) are", insert -- wherein the at least one wing is --.
Line 69, delete "that the wing(s) are", insert -- that the at least one wing is --.

Column 9,
Lines 2, 7 and 46, delete "wherein the wing(s) are", insert -- wherein the at least one wing is --.
Line 3, delete "wings tend", insert -- at least one wing tends --.
Line 8, delete "wings fall", insert -- at least one wing falls --.
Lines 12, 23, 33, 50 and 51, delete "the wing(s)", insert -- the at least one wing --.
Lines 15 and 18, delete "assemble", insert -- assembly --.
Lines 16 and 19, delete "the wing(s) are", insert -- the at least one wing is --.
Lines 26-27 and 38, delete "at least one of the wings", insert -- the at least one wing --.
Line 28, delete "of at least one of the wings", insert -- of the at least one wing --.
Line 30, delete "that wing", insert -- the at least one --.
Lines 36-37, delete "upon at least one of the wings", insert -- upon the at least one wing --.
Line 40, delete "that wing", insert -- the at least one wing --.
Line 53, delete "their own", insert -- its own --.
Line 57, delete "of each", insert -- of the at least one --.
Line 58, delete "attaching each", insert -- attaching the at least one --.

UNITED STATES PATENT AND TRADEMARK OFFICE
CERTIFICATE OF CORRECTION

PATENT NO. : 6,537,255 B1
DATED : March 25, 2003
INVENTOR(S) : Raines

It is certified that error appears in the above-identified patent and that said Letters Patent is hereby corrected as shown below:

Column 10,
Lines 37, 38, 43, 44 and 47, delete "the wing(s)", insert -- the at least one generally planar wing --.
Line 50, delete "the wings", insert -- the at least one generally planar wing --.

Signed and Sealed this

Twenty-fifth Day of April, 2006

JON W. DUDAS
*Director of the United States Patent and Trademark Office*